United States Patent [19]
Bosslet et al.

[11] Patent Number: 5,817,800
[45] Date of Patent: Oct. 6, 1998

[54] INHIBITORS OF β-GLUCURONIDASE AND THEIR USE IN THE TREATMENT OF CARCINAMATOSIS AND INFLAMMATION

[75] Inventors: Klaus Bosslet; Jörg Czech, both of Marburg, Germany; Andrea Vasella; Roland Hoos, both of Zürich, Switzerland

[73] Assignee: Hoechst Aktiengesellschaft, Frankfurt am Main, Germany

[21] Appl. No.: 904,618

[22] Filed: Aug. 1, 1997

[30] Foreign Application Priority Data

Aug. 2, 1996 [DE] Germany .................. 196 31 288.4

[51] Int. Cl.[6] .................. C07H 5/04; C07H 1/00; A61K 31/70
[52] U.S. Cl. .................. 536/53; 514/24; 514/25; 514/42; 536/4.1; 536/17.2; 536/17.9; 536/18.2; 536/22.1; 536/29.1; 536/53; 536/54; 536/55
[58] Field of Search .................. 536/4.1, 17.2, 536/17.9, 18.2, 18.7, 29.1, 22.1, 53, 54, 55; 514/24, 25, 42

[56] References Cited

U.S. PATENT DOCUMENTS

| 3,903,289 | 9/1975 | Magee ..................... 424/275 |
| 4,990,500 | 2/1991 | Vertesy et al. ............. 514/54 |
| 5,231,185 | 7/1993 | Ganem et al. ............. 546/296 |
| 5,412,082 | 5/1995 | Wittman et al. ........... 536/17.2 |

FOREIGN PATENT DOCUMENTS 0 642 799 A1  3/1995  European Pat. Off. .

OTHER PUBLICATIONS

Roland Hoos et al., "148. Synthesis and Enzymatic Evaluation of Substrates and Inhibitors of β–Glucuronidases," Helvetica Chimica Acta, vol. 79, pp. 1757–1783 (1996).

Y. Naparstek et al., "Activated T Lymphocytes Produce a Matrix–Degrading Heparan Sulphate Endoglycosidade", Nature, 310:241–244 (1984).

T. Niwa et al., "a New Potent β–Glucuronidase Inhibitor, D–Glucaro–δ–lactam Derived from Nojirimycin", J. Biochem, 72(1):207–211 (1972).

Nakajima et al., "Heparanases and Tumor Metastasis", J. of Cellular Biochemistry, 36:157–167 (1988).

*Primary Examiner*—Marian C. Knode
*Assistant Examiner*—Howard C. Lee
*Attorney, Agent, or Firm*—Finnegan, Henderson, Farabow, Garrett & Dunner, L.L.P.

[57] ABSTRACT

Compounds of the formulae I and II

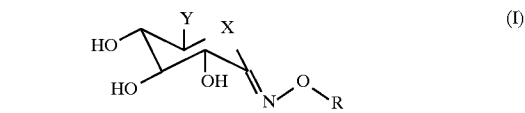

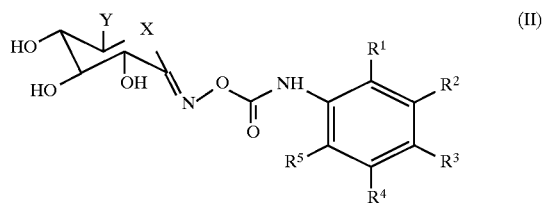

are suitable for the suppression of tumor growth and of tumor metastasis.

9 Claims, No Drawings

INHIBITORS OF β-GLUCURONIDASE AND THEIR USE IN THE TREATMENT OF CARCINAMATOSIS AND INFLAMMATION

This invention relates to the preparation of novel inhibitors of the enzyme β-glucuronidase, and their use as inhibitors of tumor growth and of metastasis, as well as for the treatment of inflammatory disorders.

β-Glucuronidases play a part in the degradation of the polysaccharide portion (glycosaminoglycans) of proteoglycans which are a main constituent of the extracellular matrix and of the endothelial basal membrane. Glycosaminoglycans (chondroitin sulfate, dermatan sulfate, heparan sulfate) contain β-glucuronic acid as a constituent which β-glucuronidases can attack exo- and endoglycolytically. It is known that activated T lymphocytes and macrophages also express heparan sulfate-degrading endoglycosidases on leaving the vascular system (Y. Naparstek et al., Nature 310, pages 241–244, 1984). It was possible to show for tumor cells that their metastatic potential is correlated with their heparanase (endo-β-glucuronidase) activity (M. Nakajima et al., Journal of Cellular Biochemistry 36: 157–167, 1988). It is furthermore known that it is possible for inhibitors of heparanase (M. Nakajima et al., Journal of Cellular Biochemistry 36: 157–167, 1988) or (exo-)β-glucuronidase (T. Niwa et al., Journal of Biochemistry 72: 207–211, 1972) to suppress the metastasis of tumors in model systems.

In spite of these findings, there is to date no inhibitor of β-glucuronidase available in the clinic for the suppression of tumor metastasis or for the treatment of inflammatory disorders.

It is therefore an object of the present invention to find novel inhibitors of β-glucuronidase which suppress tumor metastasis. There have now been found compounds of the formula I

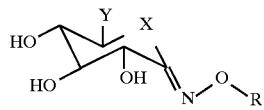

which fulfill the abovementioned criterion and wherein

Y is —COOH, —PO$_3$H$_2$, —P(O)(OR$^6$)(OH), —P(O)R$^6$(OH), tetrazole or —SO$_3$H in which R$^6$ is (C$_1$–C$_4$)-alkyl, X is NH, O or S, and R is a hydrogen atom or —C(O)NHC$_6$(R$^7$)$_5$, in which R$^7$ independently of one another is a hydrogen atom, OH, halogen, —COOH, —PO$_3$H$_2$, or —SO$_3$H.

Also included within the scope of the present invention are physiologically tolerable salts of a compound having the formula I.

Preferred compounds are those of the formula II:

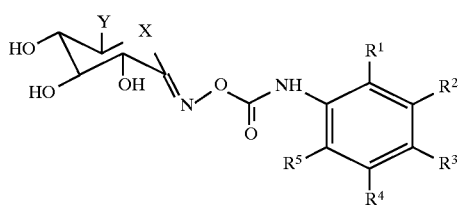

wherein

Y is —COOH, —PO$_3$H$_2$, —P(O)(OR$^6$)(OH) or —P(O)R$^6$(OH), in which

R$^6$ is (C$_1$–C$_4$)-alkyl,

X is NH or O and

R$^1$, R$^2$, R$^3$, R$^4$ and R$^5$ independently of one another are hydrogen, OH, halogen, —COOH, —PO$_3$H$_2$ or —SO$_3$H.

Also included within the scope of the present invention are physiologically tolerable salts of a compound having the formula II.

Preferred salts of the compound of the formula II are the sodium salts.

A particularly preferred compound of the formula II is one wherein

Y is —COOH or —PO$_3$H$_2$,

X is NH or O and

R$^1$, R$^2$, R$^3$, R$^4$ and R$^5$ independently of one another are a hydrogen atom or chlorine.

The compounds of the formula I or II can be prepared by processes known per se, as are described, for example, in EP 0 642 799.

The invention also relates to pharmaceuticals comprising at least one compound of the formula I or II and/or a physiologically tolerable salt of the compound of the formula I and/or II. On account of the pharmacological properties of the compounds of the formula I or II, these compounds can be employed for the treatment of carcinomatous disorders or the suppression of tumor metastasis, e.g. after operations. Furthermore, inflammatory disorders can be treated.

The invention also relates to a process for the production of a pharmaceutical, which comprises bringing the compound of the formula I or II and/or a physiologically tolerable salt of the compound of the formula I and/or II into a suitable administration form with a pharmaceutically suitable and physiologically acceptable excipient and, if appropriate, further suitable active compounds, additives or auxiliaries. The pharmaceuticals according to the invention can be administered orally, topically, rectally, intravenously or alternatively parenterally.

Suitable solid or liquid pharmaceutical preparation forms are, for example, granules, powders, coated tablets, tablets, (micro)capsules, suppositories, syrups, juices, suspensions, emulsions, drops or injectable solutions and also preparations with delayed release of active compound, in whose production customary auxiliaries, such as excipients, disintegrants, binders, coating agents, swelling agents, glidants or lubricants, flavorings, sweeteners or solubilizers are used. Frequently used auxiliaries which may be mentioned are, for example, magnesium carbonate, titanium dioxide, lactose, mannitol and other sugars, talc, lactoprotein, gelatin, starch, cellulose and its derivatives, animal and vegetable oils, polyethylene glycols and solvents, such as, for example, sterile water and mono- or polyhydric alcohols, e.g. glycerol.

Preferably, the pharmaceutical preparations are prepared and administered in dose units, each unit containing as active constituent a specific dose of the compound of the formula I or II and/or physiologically tolerable salts of these compounds. In the case of solid dose units, such as tablets, capsules or suppositories, this dose can be up to approximately 1 g.

For the treatment of an adult patient (70 kg), in early phases an intravenous infusion treatment of at most 4 g per day and in the later phase an oral administration of 3 times 1 g per day of the compound of the formula I and/or II and/or a physiologically tolerable salt of this compound are indicated.

Under certain circumstances, however, higher or lower doses may also be appropriate. The dose can be administered both by a single dose in the form of an individual dose unit or else of several smaller dose units and also by multiple administration of subdivided doses at certain intervals.

Finally, the compounds of the formula I or II and/or their corresponding salts can also be combined during the production of the abovementioned pharmaceutical administration forms together with other active compounds, for example cytostatics, protease inhibitors, neoangiogenesis inhibitors, antiinflammatory active compounds, or other inhibitors of tumor metastasis.

Inhibitors of β-glucuronidase and their syntheses are described in the following examples.

EXAMPLE 1

Synthesis of (Z)-O-(D-glucopyranuronosylidene)amino N-phenylcarbamate (sodium salt) (10):

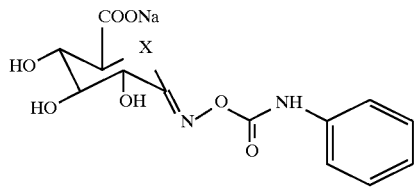
(10)

Benzyl (1,2,3,4-tetra-O-acetyl-α/β-D-glucopyran)uronate (½).

A solution of sodium glucuronate x H₂O (2.00 g, 8.54 mmol) in DMF (30 ml) was mixed with BnBr (1.5 ml, 12.6 mmol) stirred at about 23° for 24 h, filtered through Hyflo Super Cel® and treated at about 23° for 14 h with Ac₂O (20 ml) and pyridine (40 ml). Customary working up (CHCl₃, washing with H₂O, H₂SO₄, and NaHCO₃ solution) and flash chromatography (FC) (on 80 g of SiO₂) afforded ½ 1:1 (1.90 g, 49%). A sample was crystallized from Et₂O and afforded colorless crystals.

Melting point 137.5° to 139.5°.

R$_f$ (hexane/AcOEt 2:1) 0.17.

IR (CHCl₃): 2961w, 1761s, 1499w, 1456w, 1429w, 1369m, 1091m, 1041m, 913w. $^1$H—NMR (300 MHz, CDCl₃): 1.77 (1.5 H), 1.80 (1.5 H); 2.00 (3.0 H), 2.02 (1.5 H), 2.03 (1.5 H), 2.09 (1.5 H), 2.17 (1.5 H, 4 AcO); 4.22 (d, J=9.6, 0.5 H), 4.45 (d, J=10.0, 0.5 H, H—C(5)); 5.09 to 5.29 (m, 4.5 H); 5.49 (t, J≈9.9, 0.5 H); 5.77 (d, J=7.6, 0.5 H), 6.40 (d, J=3.7, 0.5 H, H—C(1)); 7.32–7.39 (m, 5 arom. H). $^{13}$C—NMR (75 MHz, CDCl₃): 20.25–20.82 (several q); 68.01 (2t); 68.87 (2d); 69.06 (d); 69.15 (d); 70.20 (d); 70.49 (d); 71.94 (d); 73.01 (d); 88.79 (d); 91.35 (d); 128.35–128.84 (several d); 134.55 (2s); 166.33 (s); 166.74 (s); 168.47 (s); 168.83 (s); 169.17 (s); 169.33 (2s); 169.52 (s); 169.89 (s), 170.00 (s). FAB-MS (3-NOBA): 475 (6, [M+Na]⁺), 394 (24), 393 (100, [M–OAc]⁺), 193 (48), 154 (22), 137 (57), 136 (29), 106 (25).

Analytical calculation for C₂₁H₂₄O₁₁ (452.41): C 55.75, H 5.35; found: C 55.66, H 5.41.

Benzyl (2,3,4-tri-O-acetyl-α/β-D-glucopyran)uronate (¾).

A solution of ½ 1:1 (6.35 g, 14.04 mmol) in DMF (100 ml) was treated with(NH₄)₂CO₃ (3.18 g) at about 22° for 4 h, cooled to 5°, and mixed with CH₂Cl₂ (200 ml) and ice (about 400 ml). Extraction with CH₂Cl₂, washing of the combined organic phases with 0.5 M H₂SO₄ and saturated aqueous NaHCO₃ solution, drying (MgSO₄), evaporation and FC (hexane/AcOEt 1:1) afforded ¾ 4:1 (3.85 g, 67%) as a colorless oil. R$_f$ (hexane/AcOEt 1:2) 0.44.

IR (CHCl₃): 3594w, 2960w, 1754s, 1498w, 1456w, 1429w, 1369m, 1146w, 1065m, 1040m, 908w.

$^1$H—NMR (200 MHz, CDCl₃) von 71/72, signals of 3: 1.77, 2.01, 2.08 (3s, 3 AcO); 3.50 (br, s, ca. 1 H, exchanged with CD₃OD, OH); 4.62 (d, J=10.1, H—C(5)); 4.92 (dd, J=10.1, 3.6, H—C(2)); 5.10 (d, J=12.0), 5.19 (d, J=12.0, PhCH₂); 5.20 (t, J≈10.1, H—C(4)); 5.55 (d, J≈3.6, addition of CD₃OD to higher fields of 0.13 ppm), H—C(1)); 5.56 (t, J≈9.7, H—C(3)); 7.35 (s, 5 arom. H). $^{13}$C—NMR (75 MHz, CDCl₃) of ¾ 4:1, signals of 3: 20.30–20.67 (several q); 67.95 (t); 67.98 (d); 69.30 (d); 69.50 (d); 70.74 (d); 90.19 (d); 128.66–128.86 (several d); 134.59 (s); 168.13 (s); 169.69 (s); 170.12 (s); 170.24 (s); signals of 72: 20.30–20.67 (several q); 68.07 (t); 69.34 (d); 71.76 (d); 72.54 (d); 72.75 (d); 95.45 (d); 128.66–128.86 (several d); 134.52 (s); 167.17–170.45 (several s). FAB-MS (3-NOBA): 433 (11, [M+Na]⁺), 394 (17), 393 (76, [M–OH]⁺), 307 (19), 303 (13), 289 (14), 193 (29), 155 (38), 154 (100).

Benzyl (E/Z)-2,3,4-tri-O-acetyl-D-glucuronate 1-oxime (⅚).

A solution of ¾ 4:1 (3.85 g, 9.38 mmol) in pyridine (55 ml) was treated with H₂NOH.HCl (1.96 g, 28.2 mmol) at about 23° for 2.5 h, diluted with CH₂Cl₂ / H₂O and shaken. The washing of the organic phase with 0.5 M H₂SO₄ and saturated aqueous NaHCO₃ solution, drying (MgSO₄), and evaporation afforded ⅚ 7:3 (3.45 g, 86%) as a yellow foam, which was further used as such.

R$_f$ (hexane/AcOEt 1:2) 0.35 (5), 0.29 (6).

IR (CHCl₃): 3573w, 3038w, 1751s, 1498w, 1456w, 1428w, 1373m, 1086m, 1045m, 958w.

$^1$H—NMR (500 MHz, CDCl₃) of ⅚ 7:3: 1.85, 1.86, 2.05, 2.09, 2.09, 2.10 (6s, 3 AcO); 3.43 (br. s, exchanged with CD₃OD, HO—C(5)); 4.21 (d, J=7.4, 0.7 H), 4.23 (d, J=6.3, 0.3 H, H—C(5)); 5.11 (d, J=11.9, 0.7 H), 5.20 (d, J≈12.1, 0.7 H); 5.14 (d, J=12.0, 0.3 H), 5.22 (d, J≈12.7, 0.3 H, PhCH₂); 5.22 (dd, J≈6.3, 5.1, 0.3 H), 5.23 (dd, J=7.4, 3.5, 0.7 H, H—C(4)); 5.56 (dd, J=7.1, 5.8, 0.7 H), 6.14 (t, J=5.7, 0.3 H, H—C(2)); 5.67 (dd, J=7.1, 3.5, 0.7 H), 5.76 (dd, J=5.6, 4.7, 0.3 H, H—C(3)); 6.55 (d, J=5.8, 0.3 H), 7.29 (d, J=5.8, 0.7 H, H—C(1)); 7.33–7.40 (m, 5 arom. H); 8.34 (br. s, exchanged with CD₃OD, 0.7 H), 8.55 (br. s, exchanged with CD₃OD, 0.3 H, NOH).

$^{13}$C—NMR (125 MHz, CDCl₃) of ⅚ 7:3, signals of 5: 20.47–20.64 (several q); 68.55 (t); 68.95 (d); 69.34 (d); 69.81 (d); 71.11 (d); 128.68–129.05 (several d); 134.37 (s); 145.50 (d); 169.60 (s); 169.81 (s); 170.20 (s); 171.81 (s); signals of 6: 65.65 (d); 68.55 (t); 69.25 (d); 69.42 (d); 71.79 (d); 134.46 (s); 146.41 (d); 169.63 (s); 169.85 (s); 170.34 (s); 171.63 (s). FAB-MS (3-NOBA): 427 (26), 426 (100, [M+1]⁺), 366 (22).

(Z)-2,3,4-Tri-O-acetyl-D-glucarhydroximo-1,5-lactone benzyl ester (7).

A solution of ⅚ 7:3 (3.15 g, about 7.41 mmol) in CH₂Cl₂ (100 ml) was treated with DBU (1.36 g, 8.93 mmol) and NCS (1.19 g, 8.91 mmol) at –78°, and warmed to about 23° in the course of 30 minutes. The solution was mixed with CH₂Cl₂ and H₂O, shaken, the phases were separated, and then the organic phase was dried (MgSO₄) and subjected to FC (on 100 g of SiO₂, hexane/AcOEt 2:1). 7 (2.40 g, 77% of ¾) was obtained as a hygroscopic foam.

R$_f$ (hexane/AcOEt 1:2) 0.33.

IR (CHCl₃): 3573w, 1760s, 1680w, 1498w, 1456w, 1372m, 1145w, 1097w, 1053m, 963w, 909w.

$^1$H—NMR (300 MHz, CDCl₃): 1.91, 2.03, 2.13 (3s, 3 AcO); 4.97 (d, J=5.5, H—C(5)); 5.18 (t, J≈3.7, H—C(3)); 5.22 (d, J=12.1), 5.28 (d, J≈12.7, PhCH₂); 5.30 (s, addition of CD₃OD→partial exchange, OH); 5.36 (dd, J≈5.0, 4.2, H—C(4)); 5.49 (d, J=3.9, H—C(2)); 7.36–7.40 (m, 5 arom. H). $^{13}$C—NMR (75 MHz, C₆D₆): 19.87 (q); 20.03 (q); 20.16 (q); 66.73 (d); 68.04 (t); 69.70 (d); 70.69 (d); 75.23 (d); 128.75 (d); 128.87 (2d); 128.94 (2d); 135.34 (s); 147.53 (s); 166.76 (s); 168.67 (s); 168.97 (s); 169.05 (s). FAB-MS (3-NOBA): 426 (6), 425 (25), 424 (100, [M+1]⁺), 307 (16).

Analytical calculation for C₁₉H₂₁NO₁₀ (423.37): C 53.90, H 5.00, N 3.31; found: C 53.37, H 5.40, N 3.39.

Benzyl O-((Z)-2,3,4-tri-O-acetyl-D-glucopyranuronosylidene)amino N-phenylcarbamate (8).

A solution of 7 (500 mg, 1.18 mmol) in CH$_2$Cl$_2$ (20 ml) was treated at 0° with PhNCO (0.25 ml, 2.29 mmol) and iPr$_2$EtN (30 ml, 0.18 mmol), immediately warmed to 23°, and stirred for 30 min. After evaporation and FC, 8 (492 mg, 77%) resulted as a foam.

R$_f$ (hexane/AcOEt 1:1) 0.36. [α]=15.4 (c=1.14, CHCl$_3$).

IR (CHCl$_3$): 3393w, 3038w, 1762s, 1670w, 1602w, 1523m, 1445m, 1372m, 1312w, 1178m, 1133w, 1101m, 1052m, 1010m.

$^1$H—NMR (300 MHz, CDCl$_3$): 1.98, 2.03, 2.18 (3s, 3 AcO); 5.03 (d, J=5.6, H—C(5)); 5.21 (t, J≈3.5, H—C(3)); 5.23 (d, J≈13.2), 5.28 (d, J=11.9, PhCH$_2$); 5.37 (dd, J≈5.6, 3.1, H-(4)); 5.64 (d, J=4.0, H—C(2)); 7.09–7.48 (m, 10 arom. H); 7.79 (br. s, NH).

$^{13}$C—NMR (75 MHz, CDCl$_3$): 20.43 (q); 20.50 (q); 20.66 (q); 65.54 (d); 68.50 (t); 68.83 (d); 69.64 (d); 75.42 (d); 119.31 (2d); 124.22 (d); 128.76 (2d); 128.82 (2d); 128.99 (d); 129.14 (2d); 134.18 (s); 136.92 (s); 150.57 (s); 150.94 (s); 165.80 (s); 168.26 (s); 168.59 (s); 168.91 (s). FAB-MS (3-NOBA): 545 (7), 544 (31), 543 (100, [M+1]$^+$), 424 (22), 423 (13), 307 (30), 289 (17).

Analytical calculation for

C$_{26}$H$_{26}$N$_2$O$_{11}$ (542.50): C 57.56, H 4.83, N 5.16; found: C 57.58, H 5.01, N 5.29.

(Z)-O-(D-Glucopyranuronosylidene)amino N-phenylcarbamate (sodium salt)(10).

A solution of 8 (255 mg, 0.47 mmol) in MeOH (6 ml) was treated at about 23° for 30 min with H$_2$ (1–2 bar) in the presence of Pd/C (10%, 5 mg). As TLC indicated the end of the reaction (new spot at R$_f$ (AcOEt/MeOH/H$_2$O 7:2:1) 0.32), a solution of NH$_3$ in MeOH (3.0 ml) was added dropwise. After 3 h, the mixture was filtered through Hyflo Super Cel® and evaporated. The residue, 9, was dissolved in H$_2$O, and filtered through a column packed with Dowexe® 50W X2 (50–100 mesh, Na$^+$form). The (Z)-O-(D-glucopyranuronosylidene)amino N-phenylcarbamate-containing fractions were collected and added to a column packed with LiChroprep® RP-18 (40–63 mm). Elution with H$_2$O, lyophilization, precipitation from MEOH with EtOH, and lyophilization afforded the sodium salt of (Z)-O-(D-glucopyranuronosylidene)amino N-phenylcarbamate (10).

R$_f$ 0.47.

IR (KBr) of 10: 3380s, 1751m, 1620s, 1550m, 1501w, 1447m, 1406w, 1318w, 1254w, 1211m, 1110w, 1062w, 1020m, 753w.

$^1$H—NMR (200 MHz, CD$_3$OD) of 9: 3.73 (dd, J=7.0, 4.9, H—C(4)); 4.02 (t, J≈5.5, H—C(3)); 4.40 (d, J=7.2, H—C(5)); 4.56 (d, J=6.1, H—C(2)); 7.01–7.09 (m, 1 arom. H); 7.25–7.33 (m, 2 arom. H); 7.42–7.52 (m, 2 arom. H). $^{13}$C—NMR (50 MHz, CD$_3$OD) of 9: 70.73 (d); 75.07 (d); 77.66 (d); 82.21 (d); 120.60 (d); 124.92 (2d); 130.21 (2d); 139.79 (s); 155.52 (s); 161.00 (s); 174.92 (s). FAB(−)-MS (glycerol) of 10: 325 (32, [M−Na$^+$]$^−$), 183 (100), 181 (41).

EXAMPLE 2

Synthesis of sodium (5R, Z)-O-(5-C-phosphonato-D-xylopyranosylidene)amino N-phenylcarbamate (9)

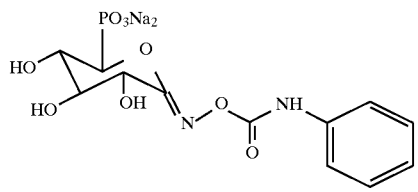

(5R)-1,2,3,4-Tetra-O-acetyl-5-C-(diphenyloxyphosphoryl)-α/β-D-xylopyranose (½).

A solution of 3-O-acetyl-1,2-O-isopropylidene-α-O-glucofuranose (60.0 g, 229 mmol) in H$_2$O (900 ml) was treated with NaIO$_4$ (55.0 g, 257 mmol), stirred for 15 min, and treated again with NaIO$_4$ (17.0 g, 79 mmol). After 1 h, the solution was extracted with CHCl$_3$ (10×300 ml), and the combined organic phases were evaporated. The residue was dissolved in CH$_2$Cl$_2$ (300 ml), mixed with freshly distilled HOP(OPh)$_2$ (53 ml, 275 mmol) and iPr$_2$EtN (2 ml, 12 mmol), stirred for 30 min and evaporated. The residue (110 g) was dissolved in AcOEt/HCO$_2$H/H$_2$O 4:4:1 (536 ml), heated under reflux for 90 min and evaporated. The residue was suspended in toluene (800 ml) and 1,4-dioxane (300 ml). H$_2$O and HCO$_2$H were removed in a Dean-Stark apparatus at about 80 mbar. After evaporation, the residue was suspended in Ac$_2$O (120 ml) and treated with 70% HClO$_4$ (4×2 ml) with vigorous shaking until a clear reddish solution formed. The solution was poured onto ice (about 600 ml), treated with pyridine (10 ml) and CHCl$_3$ (250 ml), and stirred vigorously for 60 minutes. Phase separation, extraction of the aqueous phase with CHCl$_3$ (3×250 ml), washing of the combined organic phases with saturated aqueous NaHCO3-solution (pH 11), drying (MgSO$_4$), evaporation and FC (on 800 g of SiO$_2$, hexane/AcOEt 1:1) afforded ½ 3:2 ($^1$H—NMR; 19.8 g, 16%).

Data of 1: colorless oil.

R$_f$ (hexane/AcOEt 1:1) 0.21. [α]=98.2 (c=0.62, CHCl$_3$).

IR (CHCl$_3$): 3008w, 2959w, 1758s, 1591m, 1490s, 1371m, 1161s, 1084m, 1047s, 1026m, 1010m, 986w, 957s, 986w, 957s, 906w, 838w.

FAB-MS (3-NOBA): 552 (10), 551 (33, [M+1]$^+$), 457 (21), 330 (31), 329 (100), 301 (12).

Analytical calculation for

C$_{25}$H$_{27}$O$_{12}$P (550,45): C 54.55, H 4.94; found: C 54.55, H 4.81.

Data of 2: colorless crystals. Melting point 107.0°–108.0° C. (hexane/Et$_2$O).

R$_f$ (hexane/AcOEt 1:1) 0.24. [α]=32.4 (c=0.50, CHCl$_3$).

IR (CHCl$_3$): 3008w, 1762s, 1591m, 1490s, 1369m, 1273m, 1161m, 1073s, 1040s, 1 5 958s, 906m.

FAB-MS (3-NOBA): 551 (5, [M+1]$^+$), 492 (11), 491 (40), 457 (6), 389 (12), 330 (26), 329 (100), 308 (8), 307 (30), 289 (17), 253 (14).

Analytical calculation for

C$_{25}$H$_{27}$O$_{12}$P (550.45): C 54.55, H 4.94; found: C 54.35, H 4.83.

(5R)-2,3,4-Tri-O-acetyl-5-C-(dibenzyloxyphosphoryl)-α/β-D-xylopyranose (¾).

A solution of ½ 3:2 (1 g, 3.30 mmol) in BnOH (3.7 ml) was treated at 60° with Ti(OiPr)$_4$ (0.8 ml) and stirred for about 90 min. Working up and FC (hexane/AcOEt 3:2→1:1→1:3) afforded ¾ 7:1 (341 mg, 35%).

Data of ¾: Long colorless needles. Melting point 100.5°–102.0° C. (CH$_2$Cl$_2$/hexane). R$_f$ (hexane/AcOEt 1:3) 0.25. [α]=90.2 (ca. 10 min) 73.2 (24 h) (c=1.30, CHCl$_3$).

IR (CHCl$_3$): 3550w, 3275w, 3069w, 3008m, 2962w, 1752s, 1603w, 1456m, 1369m, 1161m, 1040s, 1009s, 999s, 965m, 922w, 887w, 601m. $^{31}$P—NMR (121 MHz, CDCl$_3$) of ¾ 7:1,

Signals of 4: 17.45. FAB-MS (3-NOBA): 538 (31), 537 (100, [M+1]$^+$), 391 (22), 307 (26), 155 (18), 154 (44), 138 (23), 137 (41), 136 (33), 123 (17), 91 (54).

Analytical calculation for $C_{25}H_{29}O_{11}P$ (536.47): C 55.97, H 5.45, P 5.77 found: C 55.96, H 5.63, P 5.49.

5R, E/Z)-2,3,4-Tri-O-acetyl-5-C(dibenzyloxyphosphoryl )-D-xylose oxime (⅚).

A solution of ¾ (500 mg, 0.932 mmol) in pyridine (12.5 ml) was treated for 4 h at about 23° with $H_2NOH.HCl$ (195 mg, 2.81 mmol), diluted with $CH_2Cl_2$ and $H_2O$, and shaken. Washing of the organic layer with 0.5M $H_2SO_4$ and saturated aqueous $NaHCO_3$ solution, drying ($MgSO_4$), and evaporation afforded ⅚ (487 mg, 95%) as a yellow oil which was used immediately for the next step.

$R_f$ (hexane/AcOEt 1:4) 0.24 (5), 0.19 (6).

IR ($CHCl_3$): 3574w, 3249m, 3093w, 3069w, 3008w, 2959w, 1751s, 1603w, 1498w, 1456m, 1431w, 1373s, 1041s, 998s, 967m, 869w, 601m.

FAB-MS (3-NOBA): 552 (8, [M+1]$^+$), 189 (8), 181 (9), 171 (23), 170 (100), 136 (29).

(5R, Z)-2,3,4-Tri-O-acetyl-5-C-(dibenzyloxyphosphoryl)-D-xylanhydroximo- 1,5-lactone (7).

A solution of ⅚ (300 mg, about. 0.54 mmol) in $CH_2Cl_2$ (12 ml) was treated at −78° with a solution of DBU (95 mg, 0.62 mmol) in $CH_2Cl_2$ (3 ml) and NCS (84 mg, 0.63 mmol), and warmed to about 23° in 30 minutes. Addition of $CH_2Cl_2$ and $H_2O$, shaking, phase separation, drying of the organic phase ($MgSO_4$), and FC (on 30 g of $SiO_2$, hexane/AcOEt 1:1) afforded 7 (269 mg, 88% of ¾) as a colorless foam.

$R_f$ (hexane/AcOEt 1:2) 0.28 [α]=+50.2 (c=0.83, $CHCl_3$).
IR ($CHCl_3$): 3265w, 3008m, 175As, 1498w, 1456m, 1430w, 1374s, 1044s, 998s, 967m, 871w.

$^{31}$P—NMR (121 MHz, $CDCl_3$): 15.53.

FAB-MS (3-NOBA): 552 (9), 551 (37), 550 (100, [M+1]$^+$), 388 (10).

Analytical calculation for $C_{25}H_{28}NO_{11}P$ (549.47): C 54.65, H 5.14, N 2.55; found: C 54.37, H 5.35, N 2.33.

(5R,Z)-O-(2,3,4-Tri-O-acetyl-5-C-(dibenzyloxyphosphoryl)-D-xylo-pyranosylidene)amino N-phenylcarbamate (8).

A solution of 7 (182 mg, 0.33 mmol) in $CH_2Cl_2$ (6 ml) was treated at 0° for 30 min with PhNCO (72 ml, 0.66 mmol) and iPr$_2$EtN (30 ml, 0.18 mmol). Evaporation and FC (on 50 g of $SiO_2$, hexane/AcOEt 1:1) afforded 8 (217 mg, 98%) as a foam.

$R_f$ (hexane/AcOEt 1:2) 0.32. [α]=+53.2 (c=0.75, $CHCl_3$).
IR ($CHCl_3$): 3393w, 3008w, 2964w, 1762s, 1669m, 1602m, 1522m, 1456w, 1445m, 1373m, 1311w, 1296w, 1043s, 1008s, 996s.

FAB-MS (3-NOBA): 670 (35), 669 (100, [M+1]$^+$), 551 (20), 550 (68, [M+1−PhNCO]$^+$), 490 (25), 460 (21), 307 (27), 182 (20), 181 (39).

Analytical calculation for $C_{32}H_{33}N_2O_{12}P$ (668.59): C 57.49, H 4.97, N 4.19; found: C 57.20, H 5.15, N 4.21.

Sodium (5R,Z)-O-(5-C-phosphonato-D-xylopyranosylidene) amino N-phenylcarbamate (9).

A mixture of 8 (180 mg) and Pd/C (10%, 5 mg) in MeOH (6 ml) was treated with $H_2$ at 1 atm for 30 min and as TLC indicated the end of the reaction by the formation of a new spot at $R_f$ (AcOEt/MeOH/$H_2$O 4:2:1) 0.50, a solution of $NH_3$ in MeOH (4.5 ml) was added dropwise. After the end of the reaction (3 h), the mixture was filtered through Hyflo Super Cel®, evaporated, dissolved in $H_2O$, and filtered through a column packed with Dowex® 50W X2 50–100 mesh (Na$^+$form). The 9 fractions contained were collected and added to a column containing LiChroprepe® RP-18 (40–63 mm), which was eluted with $H_2O$. Lyophilization, precipitation from $H_2O$ with EtOH, and lyophilization afforded pure 9 (50 mg, 48%).

$R_f$ (AcOEt/MeOH/$H_2O$ 4:2:1) 0.23.

IR (KBr): 3407s, 1750m, 1654m, 1604m, 1558m, 1502w, 1447m, 1318w, 1256w, 1214m, 1082s, 976m, 907w.

$^{31}$P—NMR (162 MHz, $D_2O$): −2.63. FAB(−)-MS (glycerol): 361 (16, [M−Na+]), 275 (17), 183 (100), 181 (38).

EXAMPLE 3

Inhibition of β-glucuronidase

The inhibition of human β-glucuronidase was determined using 4-methylumbelliferyl-β-D-glucuronide as a substrate. The test mixture contained 75 μl of 2.5 mM 4-methylumbelliferyl-β-D-glucuronide, 25 μl of enzyme (0.6 μg/ml) and 10 μl of the compound of the formula I in a concentration range from 0.0001 to 100 mM, all in 200 mM sodium acetate buffer and 0.1 mg/ml bovine serum albumin (BSA), pH 5. After a 10-minute incubation at 37° C., the mixture was stopped with 1.5 ml of 0.2 M glycine/ 0.2% SDS, pH 11.7. The methylumbelliferone released by the enzyme was measured in a fluorescence photometer at 360 nm excitation and 450 nm emission wavelength.

The IC$_{50}$-values were calculated from the inhibitor dilution series using the software program GraFit 2.0 (Erithacus Software Ltd.).

|  | IC$_{50}$ (mM) |
|---|---|
| (Z)-O-(D-Glucopyranuronosylidene)amino N-phenyl-carbamate (sodium salt) (Example 1) | 0.0006 |
| Sodium (5R,Z)-O-(5-C-phosphonato-D-xylo-pyranosylidene)amino N-phenylcarbamate (Example 2) | 11 |

What is claimed is:

1. A compound of formula I

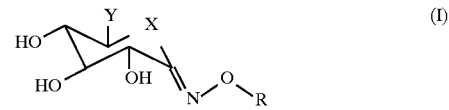

wherein
  Y is —COOH, —PO$_3$H$_2$, —P(O)(OR$^6$)(OH), —P(O)R$^6$(OH), tetrazole or —SO$_3$H in which
    R$^6$ is (C$_1$–C$_4$)-alkyl,
  X is NH, O or S, and
  R is a hydrogen atom or —C(O)NHC$_6$(R$^7$)$_5$, in which
    R$^7$ independently of one another is a hydrogen atom, OH, halogen, —COOH, —PO$_3$H$_2$, or —SO$_3$H,
or a salt of the compound of formula I.

2. A compound as claimed in claim 1, wherein said compound is a compound of formula II

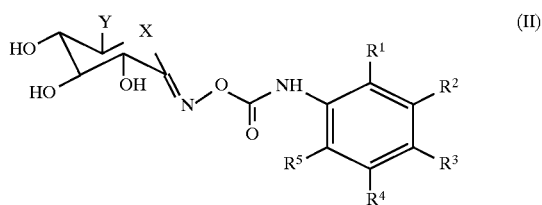

wherein
  Y is —COOH, —PO$_3$H$_2$, —P(O)(OR$^6$)(OH) or —P(O)R$^6$(OH), in which $R^6$ is $C_1$–$C_4$ alkyl X is NH or O and $R^1$, $R^2$, $R^3$, $R^4$ and $R^5$ independently of one another are hydrogen, OH, halogen, —COOH, —$PO_3H_2$ or —$SO_3H$, or a sodium salt of the compound of formula I.

3. A compound of formula II as claimed in claim 2, wherein

Y is —COOH or —$PO_3H_2$,

X is NH or O and $R^1$, $R^2$, $R^3$, $R^4$ and $R^5$ independently of one another are a hydrogen atom or chlorine.

4. A pharmaceutical composition for the treatment of carcinomatosis or inflammation comprising a pharmaceutically effective amount of at least one compound of formula I or II as claimed in any one of claims 1 to 3, or of a physiologically tolerable salt of said compound, together with a physiologically acceptable carrier.

5. A method for the treatment of carcinomatosis disorders which comprises administering to a host in need of such treatment a pharmaceutical composition as claimed in claim 4.

6. A method for the treatment of carcinomatosis disorders which comprises administering to a host in need of such treatment an effective amount of at least one compound of formula I or II as claimed in any one of claims 1–3.

7. A method for the treatment of inflammatory disorders which comprises administering to a host in need of such treatment a pharmaceutical composition as claimed in claim 4.

8. A method for the treatment of inflammatory disorders which comprises administering to a host in need of such treatment an effective amount of at least one compound of formula I or II as claimed in any one of claims 1—3.

9. A method for the production of a pharmaceutical composition for the treatment of carcinomatosis or inflammation, which comprises incorporating in said pharmaceutical composition a pharmaceutically effective amount of at least one compound of formula I or II as claimed in any one of claims 1—3.

* * * * *

UNITED STATES PATENT AND TRADEMARK OFFICE
CERTIFICATE OF CORRECTION

PATENT NO. : 5,817,800
DATED : October 6, 1998
INVENTOR(S) : BOSSLET et al.

It is certified that error appears in the above-identified patent and that said Letters Patent is hereby corrected as shown below:

On the Title Page, Item [54], in the Title, line 3, "CARCINAMATOSIS" should read --CARCINOMATOSIS--.

Claim 2, column 9, line 1, "$C_1-C_4$ alkyl" should read --$(C_1-C_4)$-alkyl--.

Claim 5, column 9, line 20, after "carcinomatosis", delete "disorders".

Claim 6, column 10, line 1, after "carcinomatosis", delete "disorders".

Signed and Sealed this

Twenty-seventh Day of July, 1999

Attest:

*Attesting Officer*

Q. TODD DICKINSON

*Acting Commissioner of Patents and Trademarks*